US00PP34670P2

(12) United States Plant Patent
van der Arend

(10) Patent No.: US PP34,670 P2
(45) Date of Patent: Oct. 18, 2022

(54) ***PHILODENDRON* PLANT NAMED 'PPIPVE015'**

(50) Latin Name: *Philodendron verrucosum*
Varietal Denomination: PPIPVE015

(71) Applicant: Rene P. A. van der Arend, Naaldwijk (NL)

(72) Inventor: Rene P. A. van der Arend, Naaldwijk (NL)

(73) Assignee: PLANT PLANET INTERNATIONAL B.V., Naaldwijk (NL)

( * ) Notice: Subject to any disclaimer, the term of this patent is extended or adjusted under 35 U.S.C. 154(b) by 0 days.

(21) Appl. No.: 17/545,677

(22) Filed: Dec. 8, 2021

(51) Int. Cl.
*A01H 5/12* (2018.01)
*A01H 6/10* (2018.01)
*A01H 5/10* (2018.01)

(52) U.S. Cl.
USPC ..... Plt./381
CPC ..... *A01H 6/10* (2018.05); *A01H 5/10* (2013.01); *A01H 5/12* (2013.01)

(58) Field of Classification Search
USPC ..... Plt./381
CPC ... A01H 5/12; A01H 5/00; A01H 5/10; A01H 6/10
See application file for complete search history.

(56) References Cited

PUBLICATIONS

National Parks Flora Fauna Web 2022, retrieved on May 4, 2022 at https://www.nparks.gov.sg/florafaunaweb/flora/6/1/6182, 6 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Philodendron* plant named 'PPIPVE015', characterized by its relatively compact, upright and uniform plant habit; moderately vigorous to vigorous growth habit; compact leaves that are dark green in color with distinct lighter green-colored venation and area adjacent to the venation.

1 Drawing Sheet

Botanical designation: *Philodendron verrucosum.*
Cultivar denomination: 'PPIPVE015'.

CROSS-REFERENCED TO A RELATED APPLICATION & STATEMENT REGARDING PRIOR DISCLOSURES BY INVENTOR/APPLICANT and ASSIGNEE This application does not claim priority to a European Community Plant Breeders' Rights application filed on Nov. 30, 2020, application number 2020/3091 and published on Feb. 15, 2021. There have been no offers for sale anywhere in the world prior to the effective filing date of this Application and no accessibility to one of ordinary skill in the art could have been derived from the printed Plant Breeder's Rights documents.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or Assignee. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Philodendron* plant, botanically known as *Philodendron verrucosum* and hereinafter referred to by the name 'PPIPVE015'.

The new *Philodendron* plant is a naturally-occurring whole plant mutation of *Philodendron verrucosum* 'PPIPVE007', disclosed in U.S. Plant Pat. No. 33,340. The new *Philodendron* plant was discovered and selected by the Inventor in December, 2019 as a single plant from within a population of plants of 'PPIPVE007' in a controlled greenhouse environment in Naaldwijk, The Netherlands.

Asexual reproduction of the new *Philodendron* plant by terminal cuttings in a controlled environment in Naaldwijk, The Netherlands since February, 2020 has shown that the unique features of this new *Philodendron* plant are stable and reproduced true to type in successive generations of asexual reproduction.

SUMMARY OF THE INVENTION

Plants of the new *Philodendron* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'PPIPVE015'. These characteristics in combination distinguish 'PPIPVE015' as a new and distinct *Philodendron* plant:

1. Relatively compact, upright and uniform plant habit.
2. Moderately vigorous to vigorous growth habit.

3. Compact leaves that are dark green in color with distinct lighter green-colored venation and area adjacent to the venation.

Plants of the new *Philodendron* differ from plants of the mutation parent, 'PPIPVE007', primarily in growth habit as plants of the new *Philodendron* are more compact plants of 'PPIPVE007'. In addition, leaves of plants of the new *Philodendron* are smaller and have more rounded apices than leaves of plants of 'PPIPVE007'.

Plants of the new *Philodendron* can be compared to plants of *Philodendron hybrida* 'Florida Green', not patented. Plants of the new *Philodendron* differ from plants of 'Florida Green' in the following characteristics:

1. Plants of the new *Philodendron* are more compact than plants of 'Florida Green'.
2. Leaves of plants of the new *Philodendron* are more rounded in shape and not as elongated as leaves of plants of 'Florida Green'.

BRIEF DESCRIPTION OF THE PHOTOGRAPH

The accompanying photograph illustrates the overall appearance of the new *Philodendron* plant showing the colors as true as it is reasonably possible to obtain in colored reproductions of this type. Colors in the photograph may differ slightly from the color values cited in the detailed botanical description which accurately describe the colors of the new *Philodendron* plant. The photograph is a side perspective view of a typical plant of 'PPIPVE015' grown in a container.

DETAILED BOTANICAL DESCRIPTION

The aforementioned photograph and following observations and measurements describe plants grown during the late autumn and early winter in 14-cm containers in a glass-covered greenhouse in Naaldwijk, The Netherlands and under cultural practices typical of commercial *Philodendron* production. During the production of the plants, day temperatures ranged from 10° C. to 25° C. and night temperatures ranged from 4° C. to 15° C. Plants were one year old when the photograph and the detailed description were taken. In the following description, color references are made to The Royal Horticultural Society Colour Chart, 2015 Edition, except where general terms of ordinary dictionary significance are used.

Botanical classification: *Philodendron verrucosum* 'PPIPVE015'.

Parentage: Naturally-occurring whole plant mutation of *Philodendron verrucosum* 'PPIPVE007', disclosed in U.S. Plant Pat. No. 33,340.

Propagation:

*Type*.—By terminal cuttings.

*Time to initiate roots, summer*.—About 20 days at temperatures about 22° C. to 25° C.

*Time to initiate roots, winter*.—About 25 days at temperatures about 20° C. to 22° C.

*Time to produce a rooted young plant, summer*.—About 45 days at temperatures about 22° C. to 25° C.

*Time to produce a rooted young plant, winter*.—About 60 days at temperatures about 20° C. to 22° C.

*Root description*.—Fibrous, medium in thickness; typically white in color, actual color of the roots is dependent on substrate composition, water quality, fertilizers, substrate temperature and age of roots.

*Rooting habit*.—Moderately freely branching; medium density.

Plant description:

*Plant and growth habit*.—Relatively compact, upright and uniform plant habit; broadly upright and roughly broadly obovate in overall shape; moderately vigorous to vigorous growth habit and moderate growth rate.

*Plant height*.—About 18.2 cm.

*Plant diameter or spread*.—About 22.1 cm.

*Stem description*.—Branching habit: Plants of the new *Philodendron* typically have a single basal shoot with an average of 1.5 lateral branches developing per plant. Length: About 7.5 cm. Diameter: About 8 mm. Internode length: About 1.8 cm. Aspect: Upright to about 25° from vertical. Strength: Strong. Texture and luster: Smooth, glabrous; initially glossy becoming slightly glossy with subsequent development. Color, developing: Close to 144B. Color, developed: Close to NN137D.

Leaf description:

*Arrangement*.—Alternate; simple.

*Length*.—About 11.8 cm.

*Width*.—About 9.6 cm.

*Shape*.—Cordate.

*Apex*.—Apiculate.

*Base*.—Cordate to hastate; lobes free to touching.

*Margin*.—Entire; slightly and coarsely undulate.

*Texture and luster, upper surface*.—Smooth, glabrous; velvety; matte.

*Texture and luster, lower surface*.—Smooth, glabrous; slightly glossy.

*Venation pattern*.—Pinnate.

*Color*.—Developing leaves, upper surface: Close to 147A; towards the base, close to 152A; veins and area adjacent to venation, close to N144C and N144D. Developing leaves, lower surface: Close to 174A and 174B; venation, close to 152C; area adjacent to venation, close to 145B. Fully expanded leaves, upper surface: Darker than between 139A and N189A; veins and area adjacent to venation, close to NN137C and NN137D. Fully expanded leaves, lower surface: Close to 166A and 174A; midvein, close to 199A and lateral venation, close to 148A; area adjacent to venation, close to 147D.

*Petioles*.—Length: About 9.5 cm. Diameter: Proximally, about 7 mm and distally, close to 5 mm. Aspect: Initially erect and then outwardly leaning. Strength: Moderately strong; flexible. Texture and luster, upper and lower surface: Distally, densely pubescent and scabrous; matte. Color, upper surface: Close to N199B. Color, lower surface: Close to 200D.

*Leaf bracts*.—Arrangement: One at the base of each petiole. Length: About 6.5 cm. Width: About 2.2 cm. Shape: Narrowly ovate with acute apex, broadly cuneate base and entire margins. Color, upper surface: Close to 51D. Color, lower surface: Close to between 173B and 174C.

Inflorescence description: To date, inflorescence initiation and development has not been observed on plants of the new *Philodendron*.

Pathogen & pest resistance: To date, plants of the new *Philodendron* not been observed to be resistant to pathogens and pests common to *Philodendron* plants.

Temperature tolerance: Plants of the new *Philodendron* have been observed to tolerate temperatures ranging from about 8° C. to about 40° C. and to be suitable for USDA Hardiness Zones 11 to 13.

It is claimed:

1. A new and distinct *Philodendron* plant named 'PPIPVE015' as illustrated and described.

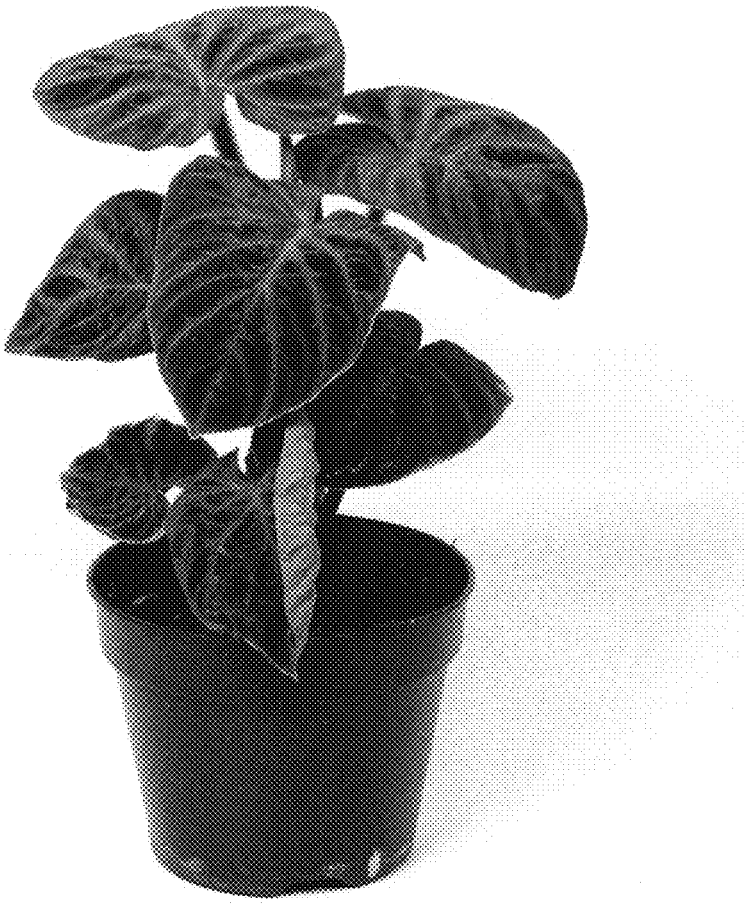

* * * * *